(12) United States Patent
Ferreira et al.

(10) Patent No.: US 6,444,442 B1
(45) Date of Patent: Sep. 3, 2002

(54) METHOD OF PRODUCING A RECOMBINANT NON-GLYCOSYLATED GP90 OF EQUINE INFECTIOUS ANEMIA VIRUS (EIAV), AND PRODUCT THEREOF

(75) Inventors: Paulo C. P. Ferreira; Erna G. Kroon; Jenner K. P. Dos Reis; Isabella B. F. Ferraz; Romulo C. Leite, all of Minas Gerais (BR)

(73) Assignee: Universidade Federal de Minas Gerais-UFMG, Belo Horizonte-Minas Gerais (BR)

( * ) Notice: Subject to any disclaimer, the term of this patent is extended or adjusted under 35 U.S.C. 154(b) by 0 days.

(21) Appl. No.: 09/582,660

(22) PCT Filed: Dec. 30, 1997

(86) PCT No.: PCT/BR97/00084

§ 371 (c)(1),
(2), (4) Date: Aug. 29, 2000

(87) PCT Pub. No.: WO99/35273

PCT Pub. Date: Jul. 15, 1999

(51) Int. Cl.[7] .................. C12N 15/20; C12N 15/48; C07K 14/15; A61K 35/74; A61K 39/21
(52) U.S. Cl. .................. 435/69.1; 435/69.3; 435/69.7; 424/187.1; 424/200.1; 530/412; 536/23.72
(58) Field of Search ............... 424/187.1, 200.1; 435/69.1, 69.3, 69.7; 530/412; 536/24.72

(56) References Cited

U.S. PATENT DOCUMENTS

| 3,929,982 A |   | 12/1975 | Coggins |
|---|---|---|---|
| 3,932,601 A |   | 1/1976 | Coggins |
| 4,806,467 A |   | 2/1989 | Porter |
| 5,310,663 A | * | 5/1994 | Dobeli et al. ............. 435/69.7 |
| 5,427,907 A |   | 6/1995 | Peterson |

OTHER PUBLICATIONS

Wang et al. Virology 1994, vol. 199, pp. 247–251.*
Kawakami et al. Virology 1987, vol. 158, pp. 300–312.*
Grund et al. J. Gen. Virol. 1996, vol. 435, pp. 435–442.*
Hussain et al. J. Virol. 1987, vol. 61, pp. 2956–2961.*

* cited by examiner

Primary Examiner—Alali R. Salimi
Assistant Examiner—Bao Qun Li
(74) Attorney, Agent, or Firm—Nixon & Vanderhye P.C.

(57) ABSTRACT

The present invention describes recombinant gp90 envelop protein derived from the equine infectious anemia virus, their corresponding encoding recombinant DNA molecule and the process of production of the recombinant protein produced through genetic engineering techniques, to be used in diagnosis, vaccination or in research.

5 Claims, 4 Drawing Sheets

Figure. 2

HisHisHisHisHisHisSerPheProGly. CysArgProPheGlnAsnTyrPheSerTyrGlu. ThrAsnArgSerMetHisMetAspAsnAsn.

ThrAlaThrLeuLeuGluAlaTyrHisArg. GluIleThrPheIleTyrLysSerSerCysThr. AspSerAspHisCysGlnGluTyrGlnCys.

LysLysValAsnLeuAsnSerSerAspSer. SerAsnSerValArgValGluAspValThr. AsnThrAlaGluTyrTrpGlyPheLysTrp.

LeuGluCysAsnGlnThrGluAsnPheLys. ThrIleLeuValProGluAsnGluMetVal. AsnIleAsnAspThrAspThrTrpIlePro.

LysGlyCysAsnGluThrTrpAlaArgVal. LysArgCysProIleAspIleLeuTyrGly. IleHisProIleArgLeuCysValGlnPro.

ProPheLeuValGlnGluLysGlyIle. AlaAspThrSerArgIleGlyAsnCysGly. ProThrIlePheLeuGlyValLeuGluAsp.

AsnLysGlyValValArgGlyAspTyrThr. AlaCysAsnValArgLeuAsnIleAsn. ArgLysAspTyrThrGlyIleTyrGlnVal.

ProIlePheTyrThrCysThrPheThrAsn. IleThrSerCysAsnAsnGluProIleIle. SerValIleMetTyrGluThrAsnGlnVal.

GlnTyrLeuLeuCysAsnAsnAsnSer. AsnAsnTyrAsnCysValValGlnSerPhe. GlyValIleGlyGlnAlaHisLeuGluLeu.

ProArgProAsnLysArgIleArgAsnGln. SerPheAsnGlnTyrAsnCysSerIleAsn. AsnLysThrGluLeuGluThrTrpLysLeu.

ValLysThrSerGlyValThrProLeuPro. IleSerSerGluAlaAsnThrGlyLeu

SEQUENCE LISTING

<160> NUMBER OF SEQ ID NOS: 5

<210> SEQ ID NO 1
<211> LENGTH: 25
<212> TYPE: DNA
<213> ORGANISM: Artificial Sequence
<220> FEATURE:
<223> OTHER INFORMATION: Description of Artificial Sequence:primer

<400> SEQUENCE: 1
cagtggatcc ttcccggggt gtaga                                        25

<210> SEQ ID NO 2
<211> LENGTH: 27
<212> TYPE: DNA
<213> ORGANISM: Artificial Sequence
<220> FEATURE:
<223> OTHER INFORMATION: Description of Artificial Sequence:primer

<400> SEQUENCE: 2
caatctgcag aattagtcca gtgttag                                      27

<210> SEQ ID NO 3
<211> LENGTH: 20
<212> TYPE: DNA
<213> ORGANISM: Artificial Sequence -continued

```
<220> FEATURE:
<223> OTHER INFORMATION: Description of Artificial Sequence:primer

<400> SEQUENCE: 3
ttcattaaag aggagaaatt                                              20

<210> SEQ ID NO 4
<211> LENGTH: 20
<212> TYPE: DNA
<213> ORGANISM: Artificial Sequence
<220> FEATURE:
<223> OTHER INFORMATION: Description of Artificial Sequence:primer

<400> SEQUENCE: 4
ctatcaacag gagtccaagc                                              20

<210> SEQ ID NO 5
<211> LENGTH: 321
<212> TYPE: PRT
<213> ORGANISM: equine infectious anemia virus

<400> SEQUENCE: 5
```

His His His His His His Ser Phe Pro Gly Cys Arg Pro Phe Gln Asn
 1               5                  10                  15

Tyr Phe Ser Tyr Glu Thr Asn Arg Ser Met His Met Asp Asn Asn Thr
            20                  25                  30

Ala Thr Leu Leu Glu Ala Tyr His Arg Glu Ile Thr Phe Ile Tyr Lys
        35                  40                  45

Ser Ser Cys Thr Asp Ser Asp His Cys Gln Glu Tyr Gln Cys Lys Lys
    50                  55                  60

Val Asn Leu Asn Ser Ser Asp Ser Ser Asn Ser Val Arg Val Glu Asp
65                  70                  75                  80

Val Thr Asn Thr Ala Glu Tyr Trp Gly Phe Lys Trp Leu Glu Cys Asn
                85                  90                  95

Gln Thr Glu Asn Phe Lys Thr Ile Leu Val Pro Glu Asn Glu Met Val
            100                 105                 110

Asn Ile Asn Asp Thr Asp Thr Trp Ile Pro Lys Gly Cys Asn Glu Thr
        115                 120                 125

Trp Ala Arg Val Lys Arg Cys Pro Ile Asp Ile Leu Tyr Gly Ile His
    130                 135                 140

Pro Ile Arg Leu Cys Val Gln Pro Pro Phe Phe Leu Val Gln Glu Lys
145                 150                 155                 160

Gly Ile Ala Asp Thr Ser Arg Ile Gly Asn Cys Gly Pro Thr Ile Phe
                165                 170                 175

Leu Gly Val Leu Glu Asp Asn Lys Gly Val Val Arg Gly Asp Tyr Thr
            180                 185                 190

Ala Cys Asn Val Arg Arg Leu Asn Ile Asn Arg Lys Asp Tyr Thr Gly
        195                 200                 205

Ile Tyr Gln Val Pro Ile Phe Tyr Thr Cys Thr Phe Thr Asn Ile Thr
    210                 215                 220

Ser Cys Asn Asn Glu Pro Ile Ile Ser Val Ile Met Tyr Glu Thr Asn
225                 230                 235                 240

Gln Val Gln Tyr Leu Leu Cys Asn Asn Asn Ser Asn Asn Tyr Asn
                245                 250                 255

Cys Val Val Gln Ser Phe Gly Val Ile Gly Gln Ala His Leu Glu Leu
            260                 265                 270

-continued

```
Pro Arg Pro Asn Lys Arg Ile Arg Asn Gln Ser Phe Asn Gln Tyr Asn
        275                 280                 285

Cys Ser Ile Asn Asn Lys Thr Glu Leu Glu Thr Trp Lys Leu Val Lys
    290                 295                 300

Thr Ser Gly Val Thr Pro Leu Pro Ile Ser Ser Glu Ala Asn Thr Gly
305                 310                 315                 320

Leu
```

METHOD OF PRODUCING A RECOMBINANT NON-GLYCOSYLATED GP90 OF EQUINE INFECTIOUS ANEMIA VIRUS (EIAV), AND PRODUCT THEREOF

TECHNICAL FIELD OF THE INVENTION

The present invention refers to the general field of the technology of the DNA recombinant proteins, for the production of the gp90 envelope protein of Equine Infectious Anemia virus (EIAV), to be used in diagnosis, vaccination, antibody production or in research field.

BACKGROUND TO THE INVENTION

The equine infectious anemia (EIA) is one of the oldest diseases caused by virus, having been described for the first time in France by LIGNEE, Rec. Med. Vet, 20:30, 1843, and recognized as viral disease by VALLEE and CARRE. Acad. Sci., 139:331–333, 1904. The disease affects exclusively the members of the family Equidae presenting a worldwide distribution and consequently of great economical importance.

The EIA virus (EIAV) is classified as a lentivirus of the Retroviridae family (CHARMAN et al. J. Virol. 19(2) :1073–1076, 1976), it is genetic and antigenically related to the other lentiviruses which are characterized by causing persistent infection. The EIA has played a specially important role in comparative virology and in the studies of the acquired immunodeficiency syndrome (AIDS). Besides their morphological identity, both viruses possess similarities in terms of nucleotide sequences that code for structural proteins, and they infect the same cells. These viruses present genetic and antigenic variants during persistent infections, which is associated to the immunologic evasion MONTAGNIER et al. Ann. Virol., 135:119–134, 1984, MONTELARO et al. J. Biol. Chem., 259:10539–10544, 1984, RUSHLOW et al. Virology, 155:309–321, 1986, STREICHER et al. J. Am. Med. Assoc. 256:2390–2391 1986, STOLER et al. J. Am. Med. Assoc. 256,2360–2364, 1986 and HAHN The transmission of EIAV occurs mainly by arthropods vectors (tabanideos) by inoculating the virus into the animal's blood stream when feeding themselves (mechanical transmission) justifying the high prevalence of EIA in hot areas favorable to the life cycle of of these vectors ISSEL et al. Vet. 17:251–286, 1988. EIA can also be transmitted by the placenta and colostro of mare with high virus titers, and by needles and surgical instruments contaminated with blood COGGINS Comparative diagnosis of viral diseases, N.Y., 4:646–658, 1981. The disease present the acute forms, subacute, chronic and mainly inaparent or assimptomaticxn ISSEL & COGGINS, J. Am. Vet. Med. Assoc. 174(7) :727–33, 1979, and the most prominent signs are the feverish episodes, anemia hemolitica, anorexia, fast weight loss and ventral edema.

Considering the high prevalence of assymptomatic carriers, the non conclusive clinical diagnosis and the possibility to confuse with other diseases as the trypanosomiases, piroplasmose, leptospirose, hepatitis and endoparasitoses the laboratory diagnosis plays a decisive role in the control and prevention of EIA.

The accepted way to diagnose the presence of EIA has been to detect the presence of antibodies specific for the disease in the serum of affected animals using the Coggins or agar gel diffusion test described in U.S. Pat. No. 3,929, 982 and U.S. Pat. No. 3,932,601. In the Coggins test, a prepared antigen is placed alongside the senum to be tested in an agar or gel medium. If EIA antibodies are present in the test serum, they will diffuse toward the antigen forming a precipitin line in the agar medium where they eventually meet. The antigen is prepared, using spleen of infected horses COGGINS & NORCROSS Cornell. Vet. 60(2) :330–5, 1970 or in culture of horse leucocytes NAKAJIMA & USHIMI Infect Immun, 3(3):373–7, 1971.

This methodology is inherently insensitive in that the EIA antigen may be contaminated with non-EIA antigens during its preparation. Antibodies against non-EIA antigens may be present in the test serum and can react Even if the prepared EIA viral antigen can be purified, the Coggins test is labor intensive and demanding of considerable expertise in interpretation of results. The Coggins test procedure is also slow to yield results, it takes twenty-four to forty-eight hours for the formation of clearly visible precipiting lines.

Porter, U.S. Pat. No. 4,806,467, discloses a method for detecting the EIA virus using a complete enzyme-linked immunoabsorbent assay incorporating a purified viral antigen and a monoclonal antibody. To obtain the antigen, the EIA virus must first be cultured. The antigen is the p26 core protein of the EIA virus and is obtained through (purification of the cultured virus by a variety of means) well known in the art. The technique of culturing a virus increases the likelihood that the assay will yeild false positive results since the virus may be contaminated with other forms of protein. Addtionally, the EIA virus is hard to culture, making the Porter approach difficult for large scale production.

The use of a synthetic peptide in an enzyme linked (immunosorbent assay) for the detection of human immunodeficiency virus (HIV) is disclosed in Shoeman, R. L. et al, Analytical Biochemistry 161:370–379 (1987). HIV and the EIA virus are members of the retrovirus family but have dissimilar structures and distinct amino acid sequences.

The main component of these preparations is therefore a protein of the virai capsid whose molecular weight is 26 KDa, (denominated p26) This is the most abundant protein of the viral particle PAREKH et al. Virology, 107:520–525, 1980, GELDERBLON, AIDS 5:617–638, 1991, and it is highly conserved within the variant samples of the isolated viruses HUSSAIN et al. J. Virol. 61:2956–2961, 1987, SALINOVICH et al. J. Virol. 57:71–80, 1986. and infected horses present specific antibodies anti-p26.

Darrel & Peisheng, the U.S. Pat. No. 5.427,907, discloses a method to use a synthetic peptide as the antigen in an immunoassay for the detection of antibodies against the equine infectious anemia virus in the serum of horses. This procedure include only the search of some epitopes of virus proteins.

It is an object of the present invention to describe the recombinant gp90 envelope protein from AIEV, their corresponding encoding recombinant DNA molecule and the process of production of the recombinant gp90 envelope protein produced through techniques of genetic engineering, to be used for diagnosis, vaccination or in research.

BRIEF DESCRIPTION OF THE DRAWINGS

These and other objects, features and many attendant advantages of the invention will be better understood upon a reading of the followng detailed description when considered in connection with the accompanying drawings wherein:

FIG. 2 shows the amino acid sequence of the recombinant gp90 envelope protein

DETAILED DESCRIPTION OF THE INVENTION

Figure 1:
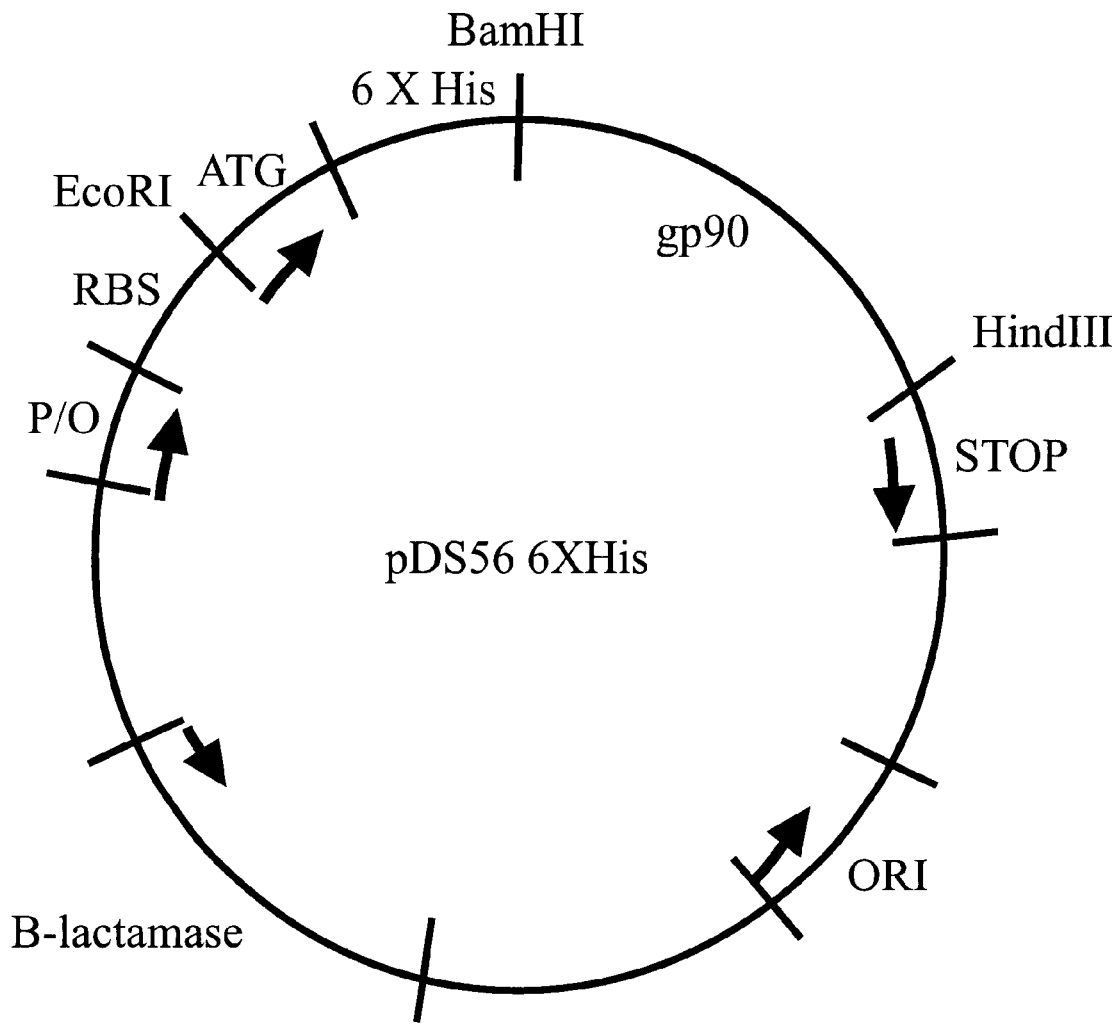
FIG. 1 shows the vector used for the expression of the recombinant gp90 envelope protein

The methodology used for the production of the recombinant gp90envelope protein consists of the cloning and expression, in microorganisms, of the DNA corresponding to the gene that codes the protein gp90 of the EIA using the methodology of the genetic engineering.

In order to better understand this invention the following examples, for illustrative purposes only, are described. The examples illustrate the present invention and are not intended to limit it in spirit or scope. The process can be understood better through the following description in consonance with the examples.

EXAMPLE 1

Virus Multiplication (1)

For multiplication of the virus cells from equine derme were used (ED) or other cells that allow replication of the virus AIE.

EXAMPLE 2

Extraction of Genomic DNA (2)

To obtain the genomic DNA (pro virus) the of cells were washed with saline STE (Tris-HCl 10–10.5 mM pH 8–8.5 NaCl 0.1 M, EDTA 1–1.5 mM). The following stage was the lysis of the cells with a solution of STE duodecil sodio (SDS sulfato) and proteinase K,(Sigma, USES) for 10–30 minutes, incubated for 50° C.–55° C. for 12–18 hours. The precipitation of the DNA was made with isopropanol and centrifuged. The pellet was homogenized in water transferred to eppendorf tube and incubated for 60° C.–65° C. for 1–2 hours for complete breakup of the DNA

EXAMPLE 3

DNA Amplification (3)

The amplification of the DNA (3) starting from the proviral DNA obtained in the stages 1, 2, or starting from the vector that contains the cloned DNA of the gene GP-90 it wascarried out using as primers the following specific oligonucleotides (SEQ ID NO: 1) 5'CAGTGGATCCT TCCCGGGGTGTAGA-3 and 5'CAATCTGCAGAATTAGTCCAGTGTTAG-3'. Those oligonucleotides were drawn to amplify, through polymerase chain reaction (PCR), the DNA region that encodes the corresponding fragment of the gp90 envelope protein. The primers also contains the sites for the restriction enzymes BamH-1 and Hind III. TCCCGGGGTGTAGA-3 and 5'CAATCTGCAGMTTAGTCCAGTGTTAG-3'. Those oligonucleotides were drawn to amplify, through polymerase chain reaction (PCR), the DNA region that encodes the corresponding fragment of the gp90 envelope protein. The primers also contains the sites for the restriction enzymes BamH-1 and Hind III.

The PCR reaction was performed with Taq polymerase buffer (50 mM KCl, 100 mM Tris-HCl pH 9.0–9.5, 1.5–2.5 mM $MgCl_2$ and 1–2% triton X-100), 0.1–1 U of Taq polymerase (Promega, E.U.A., Cat. no. M186A), 0.5–1.5 mM $MgCl_2$, 20–50 mM of each nucleotide (dATP,dCTP, dGTP,d dTTP) 10–30 μmoles of each primer, and 0.01a 0.1 μg cDNA and $H_2O$ q.s.p. 50–100 □. The reaction was performedin 1–2 cycles at 94–96° C./1–2 mi 53 to 55° C./1–2 min.; 70–72° C./1–2 min; 30 cycles at 94–96° C./1 to 2 min; 36–38° C./1–2 min; 70–72° C./1–2 min and more 1 cycle to 94–96° C./1–2 min; 36–38° C./1 to 2 min; 70–72° C./10–15 min.

The PCR product was fractionated by electrophoresis in 1.5–2.0% agarose gel and purification was made by cutting out the band of the gel. The band was diluted in 2–3 volumes of NaI solution (NaI 8M+0.022 M DTT) and sodium phosphate buffer (1M pH 6.0–6.5) and incubated for 5–10 min. at 50–56° C. Glass beads were added to the suspension, mixed incubated 1–5 min. at room temperature and centrifuged 10–30 seconds The spheres were washed with ethanol buffer (75% of ethanol, 0.01 M Tris-HCl, pH 7.0–7.6, 0.01 M EDTA, pH 8.0–8.5). The DNA was eluted from the glass spheres with buffer (Tris pH 7.0–7.4 10 mM, 1–3 mM EDTA) at 50–56° C. for 1–5 min.

EXAMPLE 4

Cloning (4)

The PCR product was digested with enzyme Hind III with 10–20 U of Hind III (Biolabs, England) plus 3–5 μl buffer (Promega,EUA) in 30–50 μl volume of $H_2O$. The reactions were incubated at 37° C. for 2–4 h. After this time 10–20 U of Bam Hi (Biolabs, England) plus 5–10 μl of react III buffer (BRL, USA) were added to a final 50–100μl volume of $H_2O$ dd and it was incubated at 37° C. for 2–4.h. For cloning of the PCR product into plasmid PDS-56 (FIG. 1), the vector vas digested with 10–20 U of enzyme Hind III (Promega, USA), 2–5 μl buffer I B (Promega, E.U.A.) in 20–50 μl final volume of $H_2O$, and incubation at 37° C. for 2–4h. To the reaction was added 10–20 U of the enzyme Bam HI (Promege, USA), 5 . 10 μl of react III (BRL, E.U.A.), in 50–100 μl final volume of $H_2O$, and incubation at 37° C. for 2–4 h. The product of this digestion was resolved in a 1% TAE-agarose gel electrophoresis. The band corresponding to the digested plasmid was cutted out of the gel, tranferred to a Eppendorf tube (1.5 ml) and pufigied.

In the ligation reaction 20–50 μg of the DNA fragment insert was added to 5–15 μg of the vector DNA, plus 0.5–2.0 U of T4 Ligase (Promega, USA), 5 mM ATP (Promega, E.U.A.), ligation buffer (Promega, E.U.A.), $H_2O$ dd qsp 15 μl, with incubation at 14–16° C. (BOD, FANEN, Brazil) for 12–18 h.

EXAMPLE 5

Transformation (5)

The bacterial transformation was done with *Escherichia coli* by adding the ligation reaction completed to 40–60 μl volume buffer (Tris 10 mM pH 7.2–7.4. EDTA 1 mM) to 100 μl of competent bacteria suspension. The tubes were slightly rotated and immediately incubated on ice bath for 20–40 min . After that, they were submitted to a thermal shock at 40–42° C. for 1–3 min. and kept on ice bath for further 20–40 seconds. LB medium (Bacto triptona 1% p/v, extract of yeast 0.5% p/v, NaCl 171 mM) without antibiotic was added at double volume and incubated at 37° C. for 1–2h. The bacteria were pelleted, homogenized in LB and inoculated in Petri dish plates with LB agar (agar 1.5% p/v, yeast extract 0.5% p/v, triptone 0.1% p/v, NaCl 0.5% piv pH 7.2–7.5) with 50–200 μg/ml ampicillin and 20–100 μg/ml kanamycin. The plates were incubated at 37° C. for 15–24 h. For the selection of the positive clones they were grown in LB with 50–200 μg/ml ampicillin and 20–100 □g/ml kanamycin at 37° C. under agitation for 15–20 h. After incubation a PCR using specific primers of the vector (for amplification of the area corresponding to insert) being the primer (sense) 5'-TTCATTAAAGAGGAGAAATT-3' (SEQ ID NO: 3) and primer (anti-sense)5'-CTATCAACAGGAGTCCAAGC-3' (SEQ ID NO: 4). The reaction was made with Taq. polymerase buffer 10X (KCl 500 mM,:Tris-HCl 100 mM pH 9.0–9.5, $MgCl_2$ 15–25 mM and triton X-100 1–2%), 0.5–1.0 U of Taq polymerase (Promega, USA), 0.5–1.5 mM $MgCl_2$, 20–50mM of each nucleotide (dATP, dCTP, dGTP, DTTP), 10–30pmoles of each primer, 0.5–1 μl of bacteriai suspension and $H_2$Odd sterile qsp 20–40 μl. The reaction was processed with 1–3 cycles of 94–96° C./5 min., 50–55° C./1–2 min., 70–72° C./1–2 min.; 30 cycles of 94–96° C./30–45 seg., 45–50° C./30–45 seg., 70–72° C./30–45 seg. and 1 cycle of 94–96° C./1–2 min., 45–50° C./1–2 min., 70–72° C./10–15 min. The product of this reaction was fractionated through 1–2%.agarose gel electrophoresis.

EXAMPLE 6

Sequencing (6)

Figure 3:
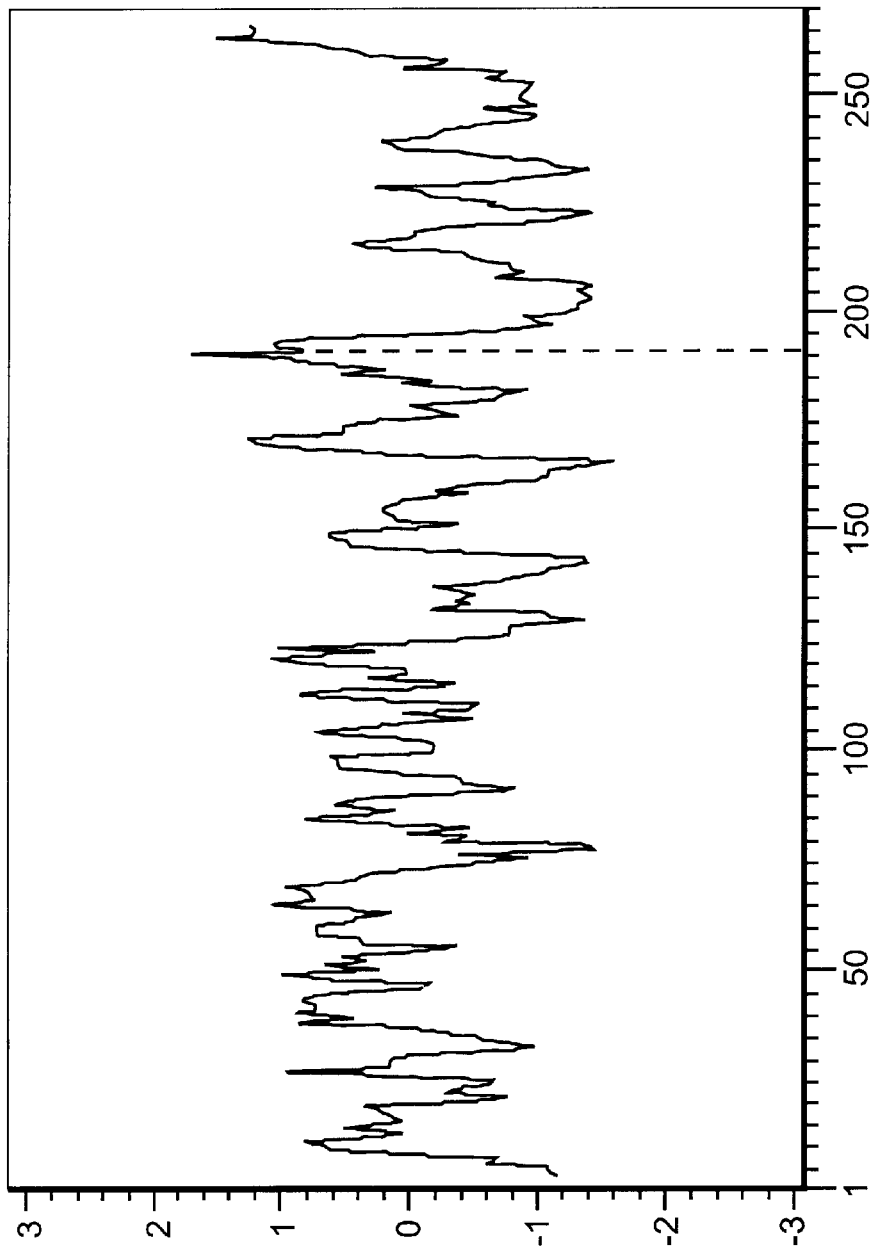
FIG. 3 shows the pattern of hydrophilicity of the recombinant gp90envelope protein

The positive clones were sequenced to confirm the sequence of FIG. 2 and presents the hydrofobicity profile as showed in FIG. 3.

EXAMPLE 7

Protein Production (7)

The positive clones were used for production of protein and they were grown in LB medium with 50–200 μg/ml ampicillin, 50–200 of Kanamycin μg/ml and incubated at 37° C. under agitation until the optical density (OD 600 nm) of 0.5–4.7. Then, for the induction of the protein, IPTG (Isopropyl-β-D-thiogalactpyranoside) to 0.2–0.4 M was added and incubated for 3–5 h. The bacteria vwere centrifuged, the supernatant was discarded and the pellet homogenized in buffer A (guanidine-HCl 5–6 M, sodium phosphate 0.1–0.2 M, Tris 0.01–0.02 M pH 7.8–8.0) with agitation for 1–2 h. A polyacrylamide gel shows the expression in the bacteria.

EXAMPLE 8

Protein Purification (8)

Figure 4:
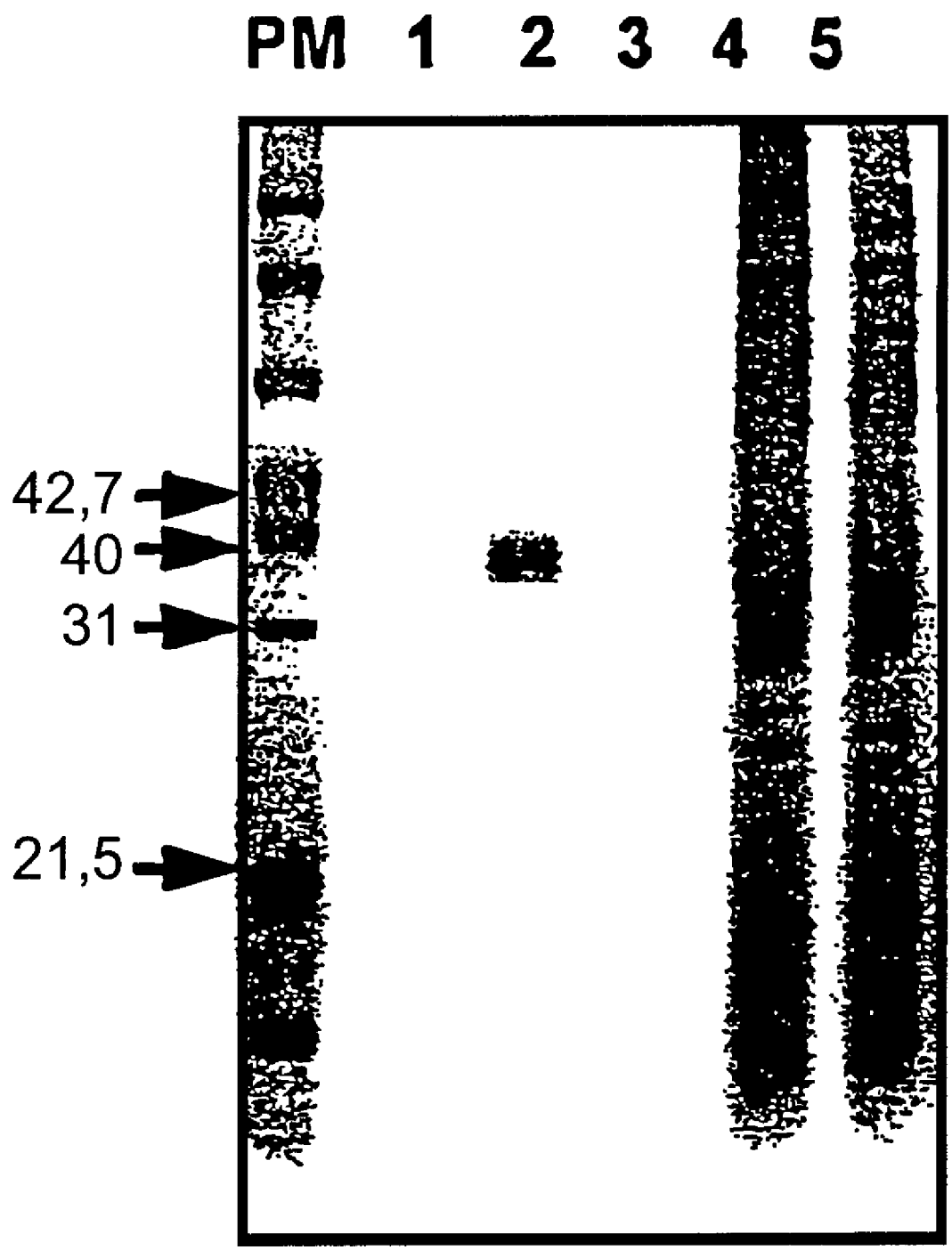
FIG. 4 shows a print of SDS-PAGE of expressed and purified recombinant gp90 protein in E. coli

After the centrifugation the supernatant was applied to a-column with Ni-NTA (nickel chelate) resin. For purification of the protein the column was washed sequentially with buffer A, buffer B (Urea 78 M, phosphate of sodium 0.1–0.2 Tris 0.01–0.02 M pH 7.8–8.0) and with buffer C (Urea 7–8 M, phosphate of sodium 0.1–0.2 M, Tris 0.01–0.02 M pH 7.0–7.2). The protein was eluter with buffer D (Urea 7–8 M, sodium phosphate 0.1–0.2 M, Tris 0.01–0.02 M pH 5.0–5.2) and sequentially with Urea 7–8 M, phosphate of sodium 0.1–0.2 M, Tris 0.01–0.02 M pH 40–4.2. Fractions were collected and 50 μl of each fraction was diluted vN in sample buffer, heated for 10 min. and submitted to electrophoresis in polyacrylamida gel (SDS-PAGE). The gel was analyzed for the presence of the fraction that just contained the band corresponding to the purified recombinant protein. (FIG. 4)

While the present invention has been described in connection with examples, it will be understood that modifications and variations apparent to those ordinary skill in the art are within the scope of the present invention.

---

What is claimed is:

1. A process for producing the recombinant gp 90 Equine Infectious Anemia envelope protein consisting of an amino acid sequence of SEQ ID NO: 5 comprising culturing in *E. coli* cell under conditions whereby said protein is produced.

2. The process according to claim 1 wherein said amino acid sequence is not glycosylated.

3. An amino acid sequence consisting of SEQ ID NO:5 produced by a process of claim 1.

4. An amino acid sequence consisting of SEQ ID NO:5 produced by a process of claim 2.

5. An amino acid sequence consisting of SEO ID NO:5 which is not glycosylated.

* * * * *